(12) United States Patent
Blizard et al.

(10) Patent No.: US 9,294,139 B1
(45) Date of Patent: Mar. 22, 2016

(54) SYSTEM AND METHODS FOR CONSTRUCTING A NOISE REPLICA

(71) Applicant: Molecular Devices, LLC, Sunnyvale, CA (US)

(72) Inventors: Benjamin Blizard, Oakland, MA (US); Michael Youngquist, Palo Alto, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 0 days.

(21) Appl. No.: 14/540,329

(22) Filed: Nov. 13, 2014

(51) Int. Cl.
*H04B 1/10* (2006.01)

(52) U.S. Cl.
CPC .................................. *H04B 1/1027* (2013.01)

(58) Field of Classification Search
CPC .. H04B 1/0017; H04B 1/0028; H04B 1/0042; H04B 1/0046; H04B 1/10
USPC .......................................... 375/254, 346, 350
See application file for complete search history.

(56) References Cited

U.S. PATENT DOCUMENTS

| | | | | |
|---|---|---|---|---|
| 5,682,307 A * | 10/1997 | Sasaki et al. | ................ | 369/44.28 |
| 5,841,809 A * | 11/1998 | Koizumi et al. | ............... | 375/233 |
| 6,215,426 B1 * | 4/2001 | Taniguchi et al. | ............ | 341/115 |
| 6,975,676 B1 * | 12/2005 | Goodson et al. | .............. | 375/231 |
| 7,076,227 B1 * | 7/2006 | Smith | ........................ | 455/278.1 |
| 7,369,833 B2 * | 5/2008 | Smith | ........................ | 455/277.2 |
| 7,630,458 B2 * | 12/2009 | Norman et al. | ............... | 375/316 |
| 7,821,437 B1 * | 10/2010 | Rud et al. | ...................... | 341/123 |
| 8,134,346 B1 * | 3/2012 | Huta | ......................... | G05F 1/70 323/211 |
| 8,139,760 B2 * | 3/2012 | Dyba et al. | ............... | 379/406.14 |
| 8,457,585 B2 * | 6/2013 | Smith et al. | ................... | 455/296 |
| 8,618,743 B2 * | 12/2013 | Miyahara | ........... | H05B 33/0806 315/185 S |
| 8,736,312 B2 * | 5/2014 | Tousignant | ......... | H03K 5/1536 327/79 |
| 8,781,030 B2 * | 7/2014 | Peng et al. | .................... | 375/327 |
| 8,786,336 B1 * | 7/2014 | Schmitt | ........................ | 327/156 |
| 2008/0200966 A1 | 8/2008 | Blomberg et al. | | |
| 2012/0065536 A1 | 3/2012 | Causevic et al. | | |
| 2014/0169581 A1 * | 6/2014 | Osako et al. | ................. | 381/73.1 |
| 2014/0222382 A1 | 8/2014 | Patel et al. | | |
| 2014/0355697 A1 * | 12/2014 | Magin | ..................... | H04L 1/004 375/257 |

FOREIGN PATENT DOCUMENTS

| | | |
|---|---|---|
| JP | 02798967 | 9/1998 |
| JP | 2011-072725 | 4/2011 |
| JP | 2012-055588 | 3/2012 |

OTHER PUBLICATIONS

Levkov et al., Removal of power-line interference from the ECG: a review of the subtraction procedure, BioMedical Engineering OnLine, 2005, 4:50, (Published: Aug. 23, 2005), http://www.ncbi.nlm.nih.gov/pmc/articles/PMC1232857/.

* cited by examiner

*Primary Examiner* — Emmanuel Bayard
(74) *Attorney, Agent, or Firm* — Bella Fishman (57) ABSTRACT

A data acquisition system and a method of operating the data acquisition system are disclosed. A zero crossing detector generates a mains cycle start signal in accordance with a power line frequency of a mains power source. An analog-to-digital converter samples a signal provided by a test probe and generates data samples at a sampling rate. A noise replica generator generates noise replicas from the data samples at a replica generation rate, and noise estimates from the noise replicas at the sampling rate, wherein the noise replica generation rate is less than the sampling frequency. A noise removal module removes each noise estimate from a corresponding data sample.

20 Claims, 11 Drawing Sheets

SYSTEM AND METHODS FOR CONSTRUCTING A NOISE REPLICA

RELATED APPLICATION

This application relates to the US Application entitled: SYSTEM AND METHOD FOR CONTROLLING LEARNING PERIOD FOR ADAPTIVE NOISE CANCELLATION." Ser. No. 14/540,299 filed on Nov. 13, 2014.

FIELD OF DISCLOSURE

The present subject matter relates to adaptive noise cancellation, and more particularly, to adaptive noise cancellation in an electrophysiology data acquisition system.

BACKGROUND

An electrophysiology data acquisition system is used in biological experiments to monitor and record electrical signals from a subject (e.g., a cell) under test. In such experiments, a researcher may use an experimental rig in which the subject is disposed. The researcher may also secure an electrode to the subject, for example, using a patch clamp technique, and then analyze the electrical signals detected by the electrode. The electrical signals from the subject may be low-level signals generated by a high-impedance signal source. As a result, such signals may be especially susceptible to electromagnetic interference (EMI) from radiated and conducted emissions of equipment connected to a mains power source. Such EMI may distort the signal of interest and appear as a "noise" or "hum" waveform added to such signal. Further, such noise may be periodic in accordance with the frequency of the electrical current generated by the mains power source. Such frequency is typically 50 hz or 60 hz and low harmonics thereof.

The researcher may use power line conditioners, Faraday cages, avoidance of "ground loops", and the like to isolate the experimental rig from environmental noise sources. Nevertheless, even when great care is taken, EMI may still be introduced in the electrical signal transmitted from the electrode to a data acquisition system. Further, if such electrical signal is affected by EMI at a time in the life cycle of the subject of interest to the researcher, the efforts of the researcher to prepare and isolate the subject may be for naught. Such EMI may result in lost time troubleshooting the experimental apparatus or, worse, in missing the time-window in which live cells must be measured and an irrecoverable loss of the cells.

SUMMARY

According to one aspect, a data acquisition system coupled to a first mains power source includes a test probe, a zero crossing detector, an analog to digital converter, noise replica generator, and a noise removal module. The zero crossing detector generates a mains cycle start signal in accordance with a power line frequency of first mains power source. The analog-to-digital converter samples a signal provided by the test probe and generates data samples at a sampling rate. The noise replica generator generates noise replicas from the data samples at a replica generation rate, and noise estimates from the noise replicas at the sampling rate, wherein the replica generation rate is less than the sampling rate. The noise removal module removes each noise estimate from a corresponding data sample.

According to another aspect, a method for operating a data acquisition system coupled to a first mains power source includes the steps of receiving a signal from a test probe, generating a mains cycle start signal in accordance with a first power line frequency of the first mains power source, sampling the signal from the test probe to generate samples of the signal at a sampling rate, and generating noise replicas from the data samples at a replica generation rate. The replica generation rate is less than the sampling rate. The method includes the further steps of developing noise estimates from the noise replicas at the first frequency, and subtracting each noise estimate from a corresponding data sample.

DETAILED DESCRIPTION

Figure 1:
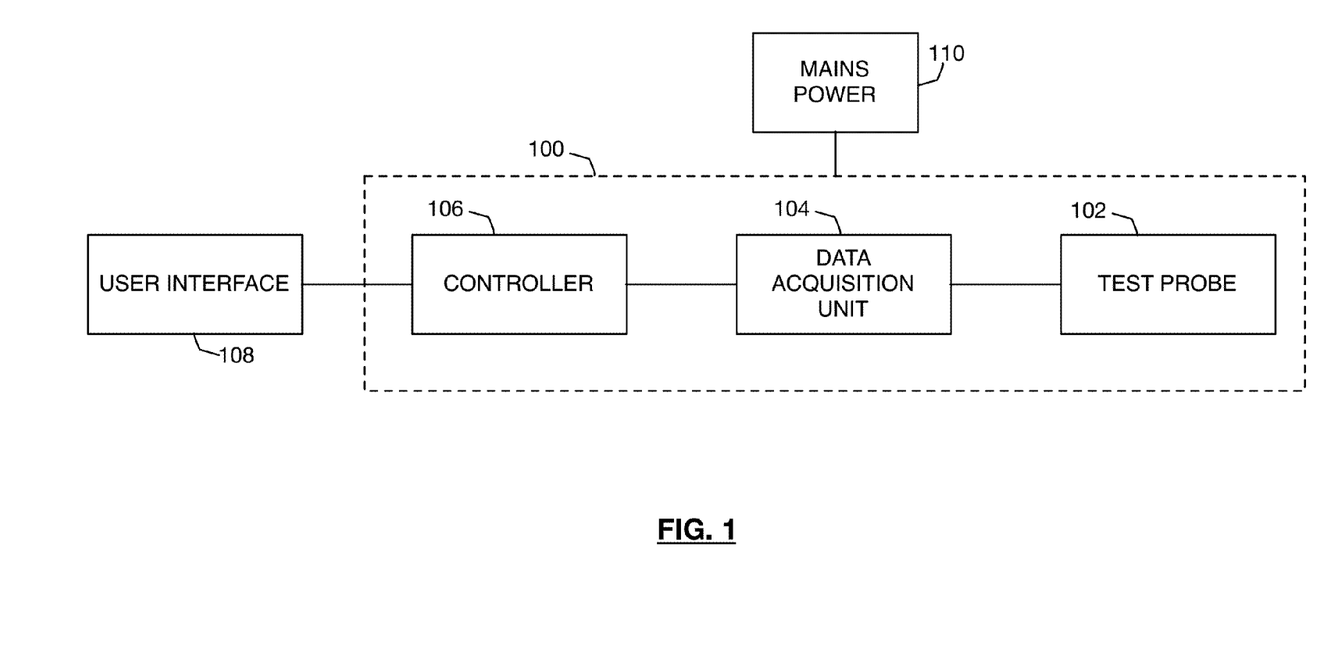
FIG. 1 is a block diagram of a data acquisition system in accordance with the present disclosure.

Referring to FIG. 1, in one embodiment an electrophysiology data acquisition system 100 includes a test probe 102, a data acquisition unit (DAU) 104, and a controller 106. In some embodiments, the system 100 is coupled to a user interface 108 provided, for example, by a computer operated by a user. The DAU 104 and other components of the system 100 may be coupled to a mains power source 110, and receive power therefrom at a predetermined power line frequency. Such power line frequency is typically location dependent and, for example, is approximately 60 Hz in the United States and approximately 50 Hz in Europe.

The test probe 102 is electrically coupled to a subject being monitored, and transduces a voltage from the subject and generates an analog signal. The DAU 104 receives the analog signal from the test probe 102, samples the analog signal to generate digital samples of the analog signal, and processes the digital samples to remove noise components therefrom and generates noise corrected output samples. The controller 106 may display such noise corrected output samples on the user interface 108, store such noise corrected output samples on a storage medium (not shown) associated with the system 100, or transmit such noise corrected output samples to another device or system (not shown). The user interface 108 may be directly coupled to the system 100 or may be coupled to the system 100 using a private or public network. Similarly, the storage medium may be directly coupled to the system 100 or may be coupled using a private or public network.

The user uses the user interface 108 to supply to the controller 106 directives to configure the DAU 104 and/or the test probe 102, to initiate sampling of the signals developed by the test probe, and to either store and or display the noise corrected samples. The controller interprets such directives and coordinates the operation of the DAU 104 and/or the test probe 102 accordingly.

Figure 2:
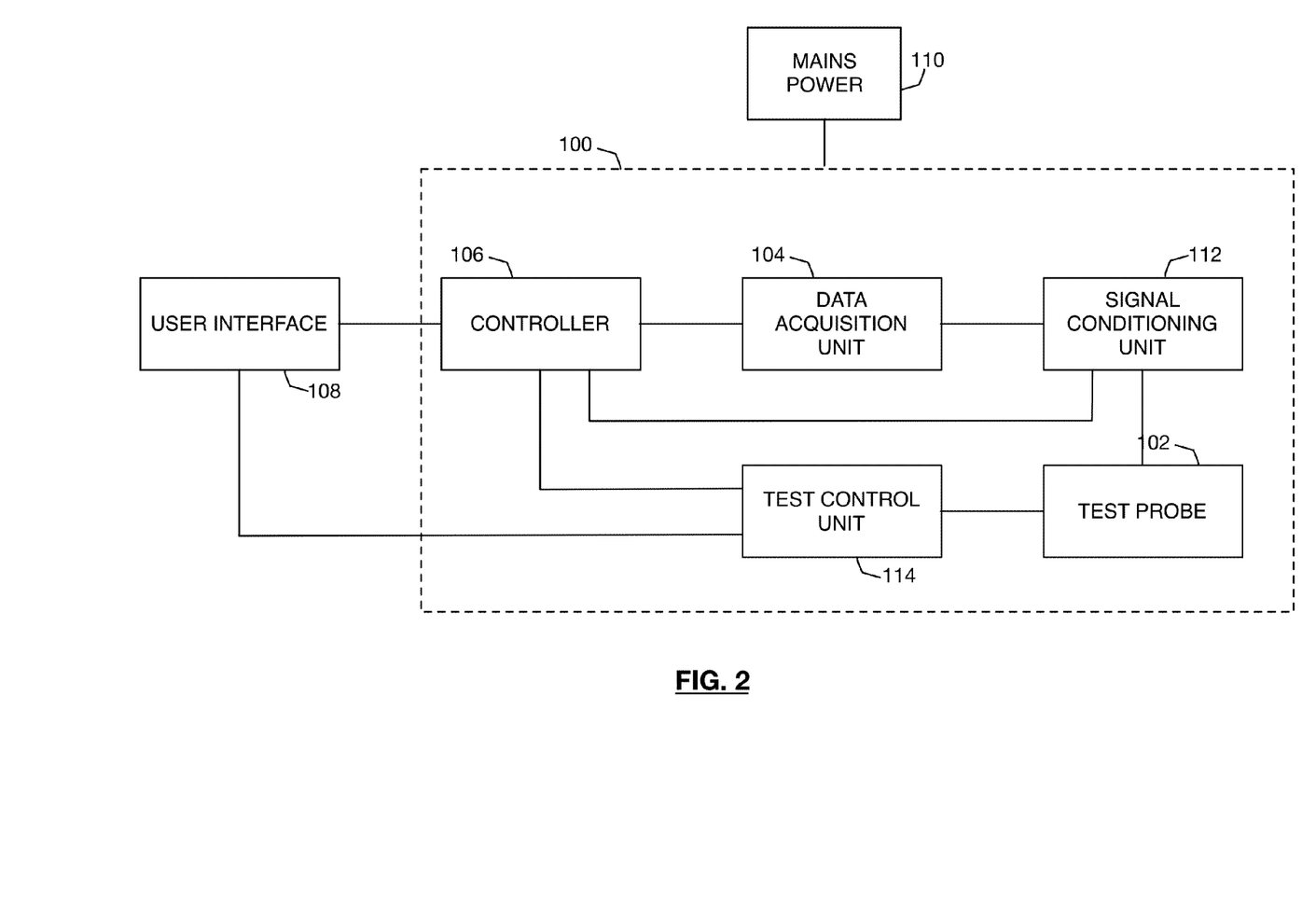
FIG. 2 is a block diagram of another embodiment of the data acquisition system of FIG. 1.

Referring to FIG. 2, in some embodiments, the system 100 may further include a signal conditioning unit 112 and/or a test control unit 114. The signal conditioning unit 112 may include for example a passive or active amplifier to amplify the analog signal from the test probe and supply the amplified signal to the DAU 104. In some embodiments, the user may control gain of the amplifier by, for example, operating a knob or a dial, one or more switches, or a slide control disposed on a housing (not shown) in which one or more components of the system 100 are disposed. Alternately, the controller 106 may, for example, control such amplifier electronically, in response to commands received from the user interface 108. In some embodiments, the test probe 102 and the signal conditioning unit 112 may be integrated into a single unit that is electrically coupled to other components of the system 100.

The test control unit 114 may include a device that may stimulate the subject being monitored. Such stimulation may include exposing the subject to a chemical or a drug from one or more micro-pipettes, delivering an electrical voltage, exposing the subject to a visible or invisible light source, generating a sound, and the like. In some embodiments, the user interface 108 may directly control the test control unit 114. In other embodiments, the controller 106 may receive directives from the user interface 108 regarding the stimulation to be provided, and the controller 106 actuates the test control unit 114 accordingly.

Figure 3:
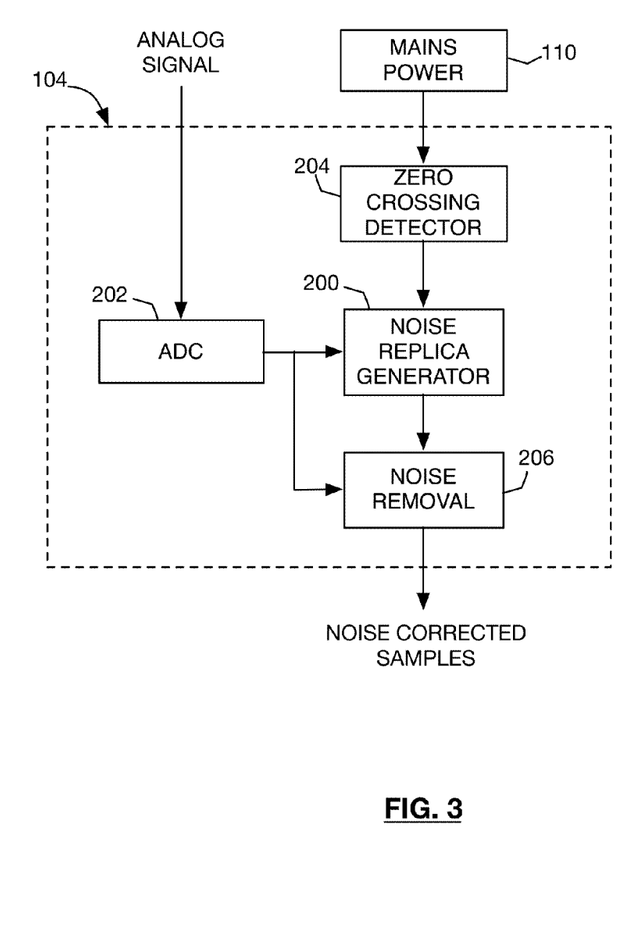
FIG. 3 is a block diagram of a data acquisition unit of the data acquisition system of FIG. 1.

Referring to FIG. 3, an embodiment of the DAU 104 includes a noise replica generator 200, an analog-to-digital converter (ADC) 202, a zero-crossing detector (ZCD) 204, and a noise removal module 206. The analog-to-digital converter 200 converts the analog signal from the test probe 102, and simultaneously provides digital samples to both the noise replica generator 200 and the noise removal module 206. The ADC 202 operates to provide a sample of the analog signal at a predetermined sampling frequency or sampling rate. In some embodiments the ADC 202 generates samples at a rate of 500 kilo-samples/second. Each time the ADC 202 generates a sample, the noise replica generator 200 supplies to the noise removal module 206 an estimate of the noise in such sample. The noise removal module 206 subtracts such noise estimate from the sample and generates a noise corrected sample.

The ZCD 204 monitors the voltage supplied by the mains power source 110 and generates a zero-crossing signal in accordance with the power line frequency of such voltage. It should be apparent to those who have skill in the art that a debounce filter or circuit may condition the signal from the mains power source 110 and the ZCD 104 monitors the voltage in such conditioned signal. In some embodiments, if the DAU 104 is operated in the United States, the ZCD 204 generates a zero-crossing signal 120 times-per-second in accordance with the 60 Hz power line frequency used in the United States. Similarly, if the DAU 104 is operated in Europe, the ZCD 204 may generate a zero-crossing signal 100 times-per-second in accordance with 50 Hz power line used there. In other embodiments, the ZCD 204 may generate a signal only in response to a positive to negative voltage transition in the mains power source 110, and therefore, generates a zero-crossing signal either 60 times-per-second in the United States and 50 times-per-second in Europe. Alternately, the ZCD 204 may generate a signal only in response to a negative to positive voltage transition in the mains power source 110.

In one embodiment, the ZCD 204 includes an analog to digital converter (not shown) that samples a power line voltage supplied by the mains power source 110, and analyzes that waveform represented by such samples to find the zero crossing. In another embodiment, the ZCD 204 may determine the zero crossing using a transformer and a comparator, or an optocoupler and comparator, as would be apparent to those who have skill in the art. Other ways of developing the zero-crossing signal apparent to those who have skill in the art may be used.

Although the zero-crossing signal generated by the ZCD 204 described represents a time when the voltage of the power line is zero, one of skill in the art should understand the zero-crossing signal may be generated when the power line is at any predefined voltage that indicates a start of a cycle of periodic waveform associated with the power line. The zero-crossing signal indicates any consistent position of such waveform. For example, a zero-crossing signal may be generated at 0.2476 volts in the positive going direction or 88.32 volts in the negative going direction or any other value that is reached or crossed during each cycle of the mains. The zero-crossing signal generated by the ZCD 204 may be any signal that can be use to synchronize the phase of the components of the noise replica generator 200 to that of the mains power source 110. As such, the zero-crossing signal generated by the ZCD 204 is a mains cycle start signal.

As described below, the noise replica generator 200 synchronizes the operation thereof with the zero-crossing signal developed the ZCD 204 to generate an estimate noise induced by EMI in the mains power source 110 in the samples generated by the ADC 202. In this manner, the system 100 may be used without modification in different countries having different mains sources that supply power at different power line frequencies.

Figure 4:
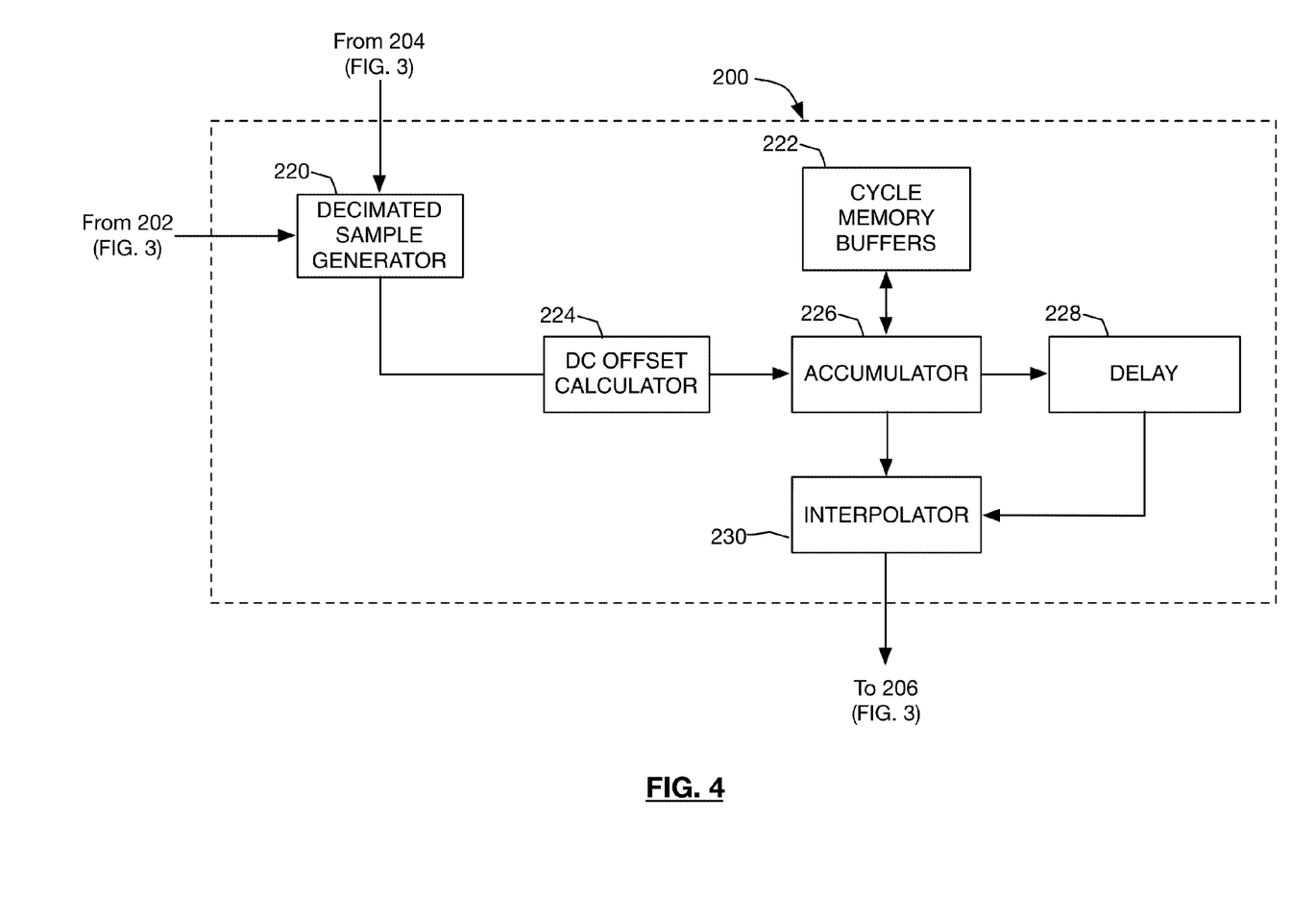
FIG. 4 is a block diagram of a noise replica generator of the data acquisition unit of FIG. 3.

Referring to FIG. 4, the noise replica generator 200 comprises a decimated sample generator 220, a plurality of cycle memory buffers 222, a DC offset calculator 224, an accumulator 226, a delay 228, and an interpolator 230.

The decimated sample generator 220 of the noise replica generator 200 decimates (i.e., sub-samples) the samples generated by the ADC 202 by a predetermined decimation factor. In some embodiments, the predetermined decimation factor is 25 and the decimated sample generator 220 selects every $25^{th}$ sample generated by the ADC 202 and provides the selected decimated sample to a DC offset calculator 224. The decimated sample generator 220 generates decimated samples at a rate that is the sampling rate of the ADC 202 divided by the decimation factor.

It should be apparent to those who have skill in the art that the ADC 202 may be adapted to provide a sample to noise removal block 206 at the sampling rate (e.g., 500 kilo-samples/second) of the ADC 202, and select samples in accordance with the decimation factor to provide to the noise replica generator 200. In such embodiments, a separate decimated sample generator 220 may not be used in the noise replica generator 200.

Figure 5:
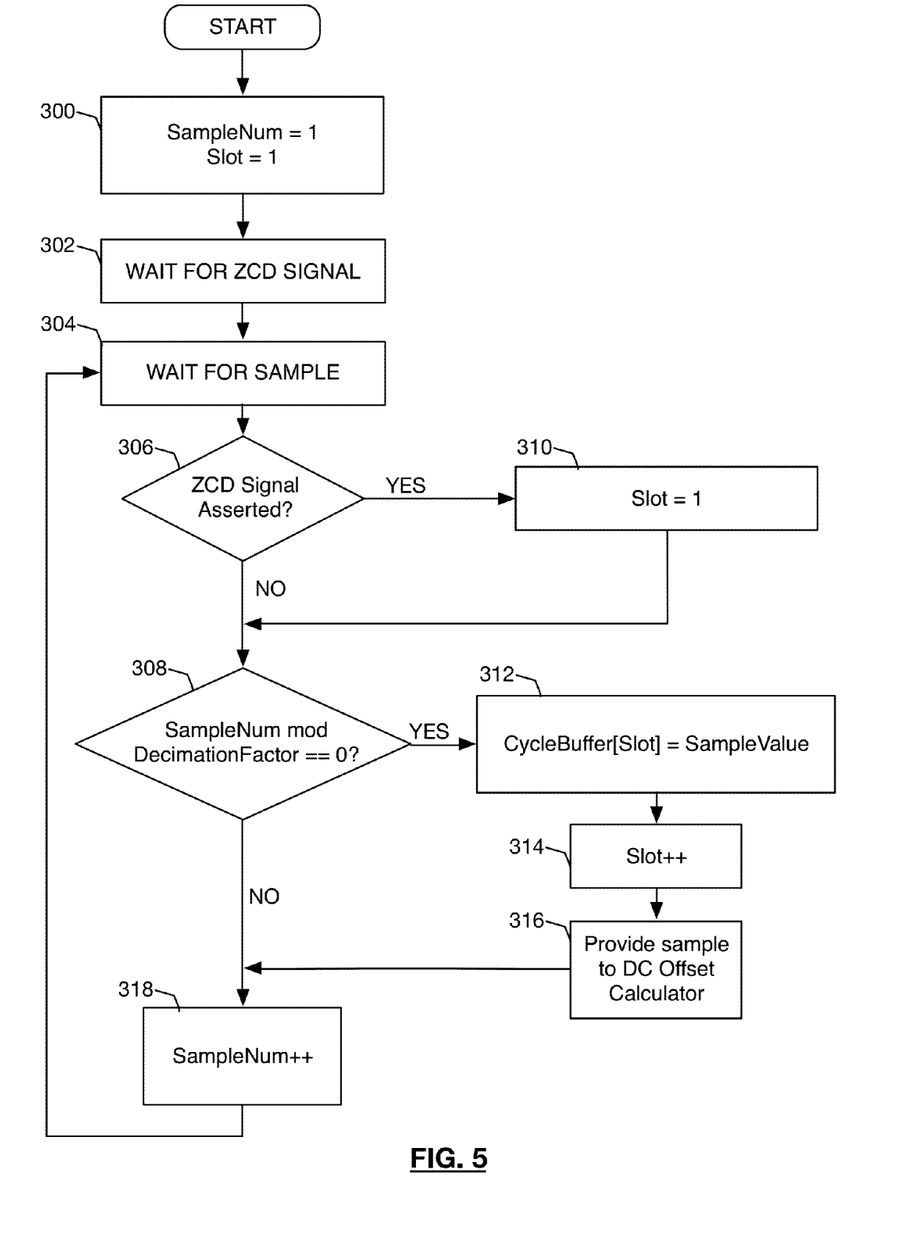
FIG. 5 is a flowchart of processing undertaken by a decimated sample generator of the noise replica generator of FIG. 4 to decimate samples of a signal.

Referring to FIGS. 4 and 5, when started, the decimated sample generator 220, at block 300, initializes the values of the variables SampleNum, and Slot, which represent the number of the sample received, and the slot of the a buffer where such decimated sample is to be stored, respectively. At block 302, the decimated sample generator 220 waits for a zero-crossing signal to be generated, and thereafter, at block 304, waits for a sample to be received from the ADC 202. Then at block 306, the decimated sample generator 220 determines if a zero-crossing signal was generated between receipt of a previous sample from the ADC 202 and the sample just received at block 306. If no such signal was generated, the decimated sample generator 220 proceeds to block 308.

Otherwise, at block 310, decimated sample generator 222 also sets the value of the variable Slot to one, at block 310. Thereafter, the decimated sample generator 220 proceeds to block 308.

At block 308, the decimated sample generator 220 determines if the sample received at block 304 should be selected as a decimated sample. In particular, if the modulo of the value of the variable SampleNum and the decimation faction is zero, the received sample is selected, and the decimated sample generator 220 proceeds to block 312. Otherwise the value of the variable SampleNum is incremented, at block 318, and the decimated sample generator 222 proceeds to block 304 to wait for another sample.

If, at block 308, the decimated sample generator 220 determines that the sample received at block 304 should be selected as a decimated sample, the decimated sample generator 220, at block 312, stores the selected sample in the buffer at a location within such buffer referenced by the value of the variable Slot. Thereafter, the decimated sample generator 220 increments the value of the variable Slot by one at block 314, and provides the selected sample to the DC offset calculator 224. The decimated sample generator then proceeds to block 318.

The DC offset calculator 224 calculates a rolling average of decimated samples generated over one periodic cycle of the power line the mains power source 110. The DC offset calculator 224 includes an internal ring buffer (also referred to as a "cyclic" or "rolling" buffer) that is large enough to store a number of decimated values that may be generated over one periodic cycle of the mains power source 110. The maximum ring buffer size may be determined from the minimum acceptable frequency of the mains power source 110 and the decimation factor. It should be apparent to those who have skill in the art that the ring buffer size increases as the frequency of the mains power source 110 decreases. Each time the decimated sample is received from the decimated sample generator 220, the decimated sample is added to the ring buffer. In addition, each time such decimated sample is received, the DC offset calculator 224 averages the values stored in the ring buffer. That is, the DC offset calculator 224 calculates a sum of the values stored in the ring buffer, and then divides such sum by the number of such values. The DC offset calculator 224 then subtracts the calculated average from the received decimated sample to estimate the noise in the received decimated sample. The DC offset calculator 224 supplies such estimate of the noise in the decimated sample to the accumulator 226 and the interpolator 230. In some embodiments, DC offset calculator 224 also receives an indication that the ZCD 204 has detected a zero-crossing of the mains power source 110. Such indication may be, for example, a flag set the ZCD 204 or a signal sent to the DC offset calculator 224. The DC offset calculator 224 counts the number of decimated samples received between successive detections of the zero-crossing to determine the number of decimated samples to include in each average generated thereby. Further, if the sampling frequency is not an integral multiple of the decimation frequency, the DC offset calculator 224 may include in the average, a value interpolated between a last decimated value generated in a periodic cycle of the mains power source 110 and a first decimated value generated in a successive period cycle of the mains power source 110. For example, if the ADC 202 sampling rate is 500 kilo-samples per second, the mains power frequency is 60 Hz, and the decimation rate is one sample every 25 samples, then the decimation frequency Is 333⅓ decimated samples per 60 Hz cycle. The DC offset calculator uses interpolation as described above to account for the effect of the ⅓ decimated sample in the DC offset calculated thereby.

The accumulator 226, receives the estimate of the noise from the DC offset calculator 224. The accumulator 226 uses a predetermined number of cycle memory buffers 222, each cycle estimate buffer 222 having sufficient space to store the noise estimates of decimated values that may be developed in one periodic cycle of the mains power source 110. The received noise estimates from the DC offset calculator 224 are stored in these cycle memory buffers 222 in a rolling fashion. In addition, the accumulator 226 includes a noise replica buffer that is at least large enough to hold the number of noise estimates that may be generated during one periodic cycle of the mains power source 110.

Each cycle memory buffer 222 is associated with one periodic cycle of the mains power source 110. Each location in a particular cycle memory buffer 222 is associated with a decimated sample time within such periodic cycle when a decimated sample value is supplied by the decimated sample generator 220. For example, for a particular periodic cycle, the first decimated sample value generated may be stored in a first location of the cycle memory buffer 222 associated with such cycle, and a second decimated sample value generated may be stored in a second location in such buffer, and so on. When all of the decimated sample values are generated for the cycle, the values from the next cycle are stored in another buffer of the cycle memory buffers 222. When all of the cycle memory buffers 222 are filled, additional noise estimate values received replace the oldest noise estimate values in the cycle memory buffers 222.

In one embodiment, the accumulator 226 includes fifty such cycle memory buffers 222. After fifty cycles worth of decimated samples are stored in such buffers, further values replace the oldest decimated values. In this manner, the accumulator 226 maintains the noise estimate values generated during the fifty most recent cycles of the mains power source 110.

The noise replica buffer includes one location associated with each decimated sample that is generated during one periodic cycle of the mains power source 110. When a noise estimate is received, the value of such noise estimate is added to the value in the location in the noise replica buffer associated with the decimated sample time associated with the received value. In addition, the value of the oldest noise estimate associated with such decimated sample time in the cycle memory buffers 222 is subtracted from the noise estimate to generate a current noise replica. The accumulator 226 provides the current noise replica to the delay 228 and the interpolator 230. The accumulator 226 provides the current noise replica to the delay 228 and the interpolator 230 at a rate (i.e., a noise replica generation rate) that may be the sampling rate of the ADC 202 divided by the decimation factor used by the decimated sample generator 220.

Figure 6:
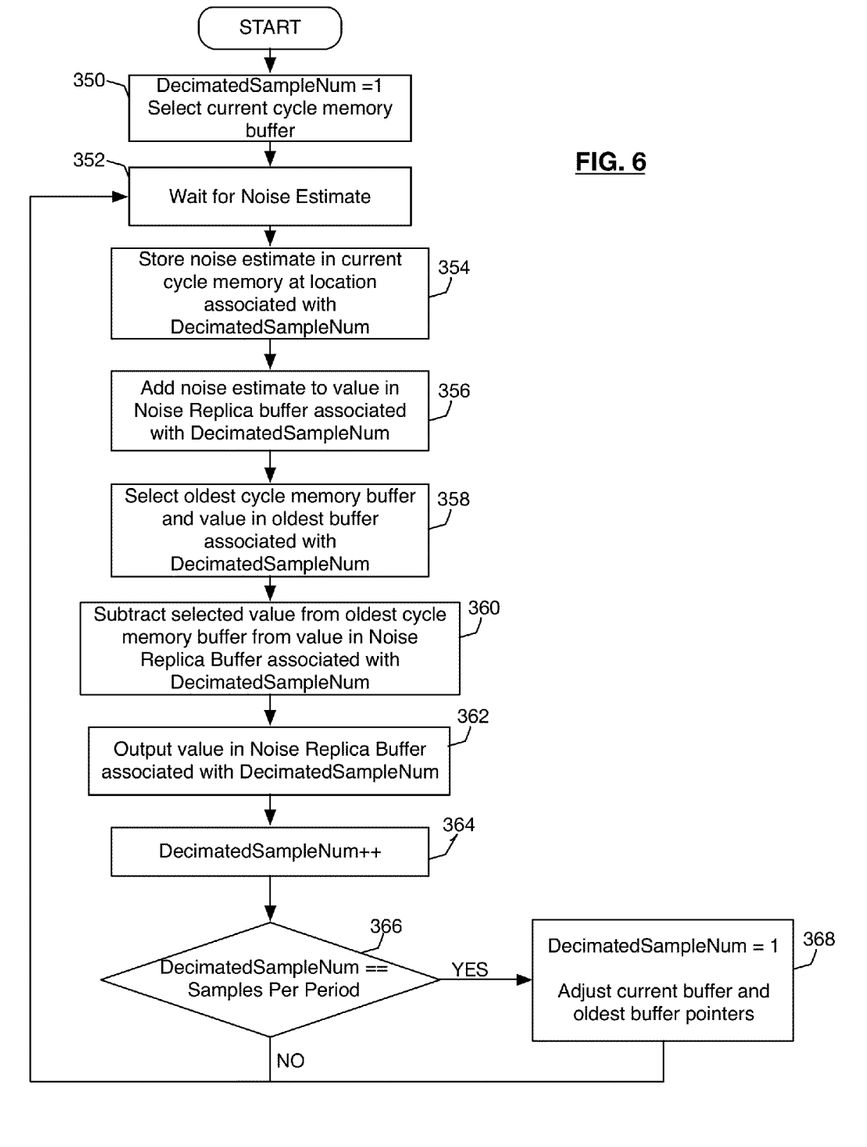
FIG. 6 is a flowchart of processing undertaken by an accumulator of the noise replica generator of FIG. 4 to develop a noise replica.

Referring to FIGS. 4 and 6, the accumulator 226, when started, selects at block 350 a current cycle memory buffer 222 into which received noise estimate will be stored, and sets a value of a variable DecimatedSampleNum that counts the number of samples received within one periodic cycle of the mains power source 110. Thereafter, the accumulator 226 waits at block 352 for a noise estimate to be generated by the DC offset calculator 224. When the noise estimate is received, the accumulator 226, at block 354, stores the received noise estimate in a location of the current cycle memory buffer 222 that is associated with the value of the variable DecimatedSampleNum.

Thereafter, at block 356, the accumulator 226 adds the value of the received noise estimate to a value in the noise replica buffer that is stored in a location associated with the variable DecimatedSampleNum. At block 358, the accumulator 226 selects the cycle memory buffer 222 that has the oldest received noise estimates, and selects a value stored in such buffer that is associated with the variable DecimatedSampleNum. At block 360, the accumulator subtracts the value selected at block 358 from the value of the noise replica buffer associated with the variable DecimatedSampleNum to develop the current noise replica. At block 362 the accumulator 226 supplies the current noise replica to the delay 228 and the interpolator 230.

Thereafter, the accumulator 226 increments the value of the variable DecimatedSampleNum at block 364. The accumulator 226 then determines if the incremented DecimatedSampleNum is equal to number of decimated samples generated in one periodic cycle of the mains power source 110. If not, the accumulator 226 proceeds to 352 to wait for the next noise estimate. Otherwise, the accumulator 226 resets the value of the variable DecimatedSampleNum to one, and sets another of the noise buffers to be the current cycle memory buffer 222, and identifies the cycle memory buffer 222 in which the oldest noise estimates are stored, at block 368. Thereafter, the accumulator 226 proceeds to block 352. In this manner, each replica generated by the accumulator 226 in response to a decimated value received at a particular decimated sample time within a periodic cycle is based on noise estimate values associated with the decimate sample time stored in the cycle memory buffers 222.

Returning to FIG. 4, the delay 228 is a one periodic cycle delay circuit. In particular, the delay 230 holds a noise estimate received value from the accumulator 226 until a further value is received from the accumulator 226.

Figure 7:
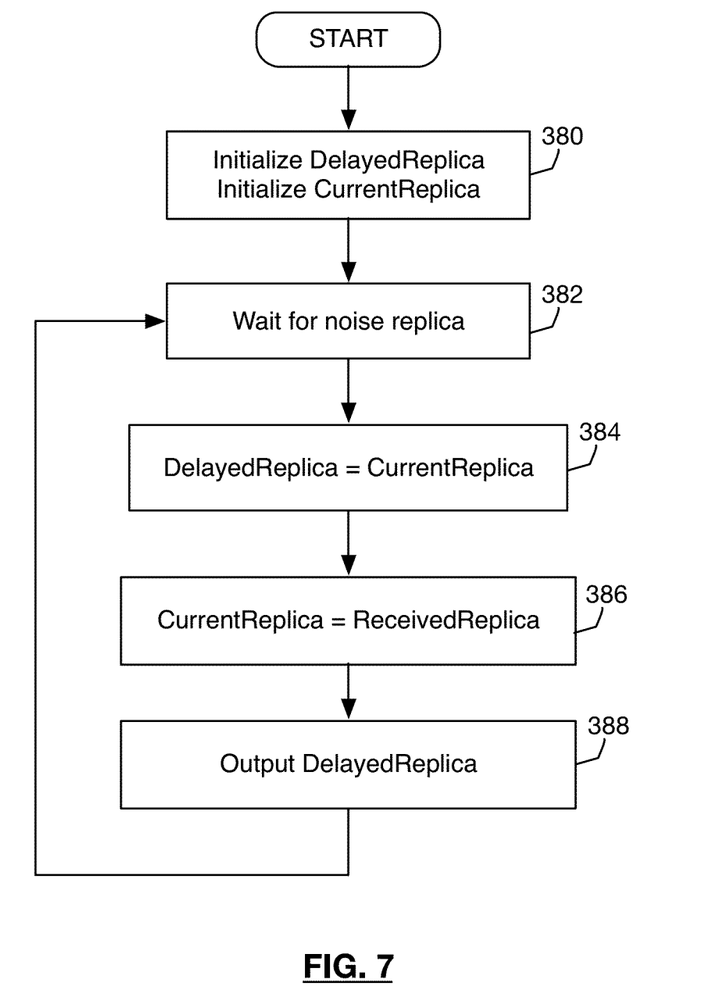
FIG. 7 is a flowchart of processing undertaken by a delay of the noise replica generator of FIG. 4.

Referring to FIG. 7, when started, the delay 228 at block 380, initializes values of variables DelayedReplica and CurrentReplica to predetermined values, for example, zero. At block 382, the delay 228 waits to receive a noise replica from the accumulator 226. At block 384, the delay 228 sets the value of the variable DelayedReplica to the value of the variable CurrentReplica. Then, at block 386, the delay 228 stores the value of the noise replica received at block 382 in the variable CurrentReplica. The delay 228 outputs the value of the DelayedReplica at block 388 and proceeds to block 382 to wait for another noise replica.

Returning to FIG. 4, the interpolator 230 receives a current noise replica from the accumulator 226 and a delayed (i.e., previous) noise replica from the delay 228. Note that the current noise replica and the delayed noise replica are generated at the decimation frequency used by the Decimated Sample Generator 220. The interpolator 230 interpolates between these two noise replicas to generate sequential noise estimates at a frequency at which the ADC 202 samples the input signal.

Figure 8:
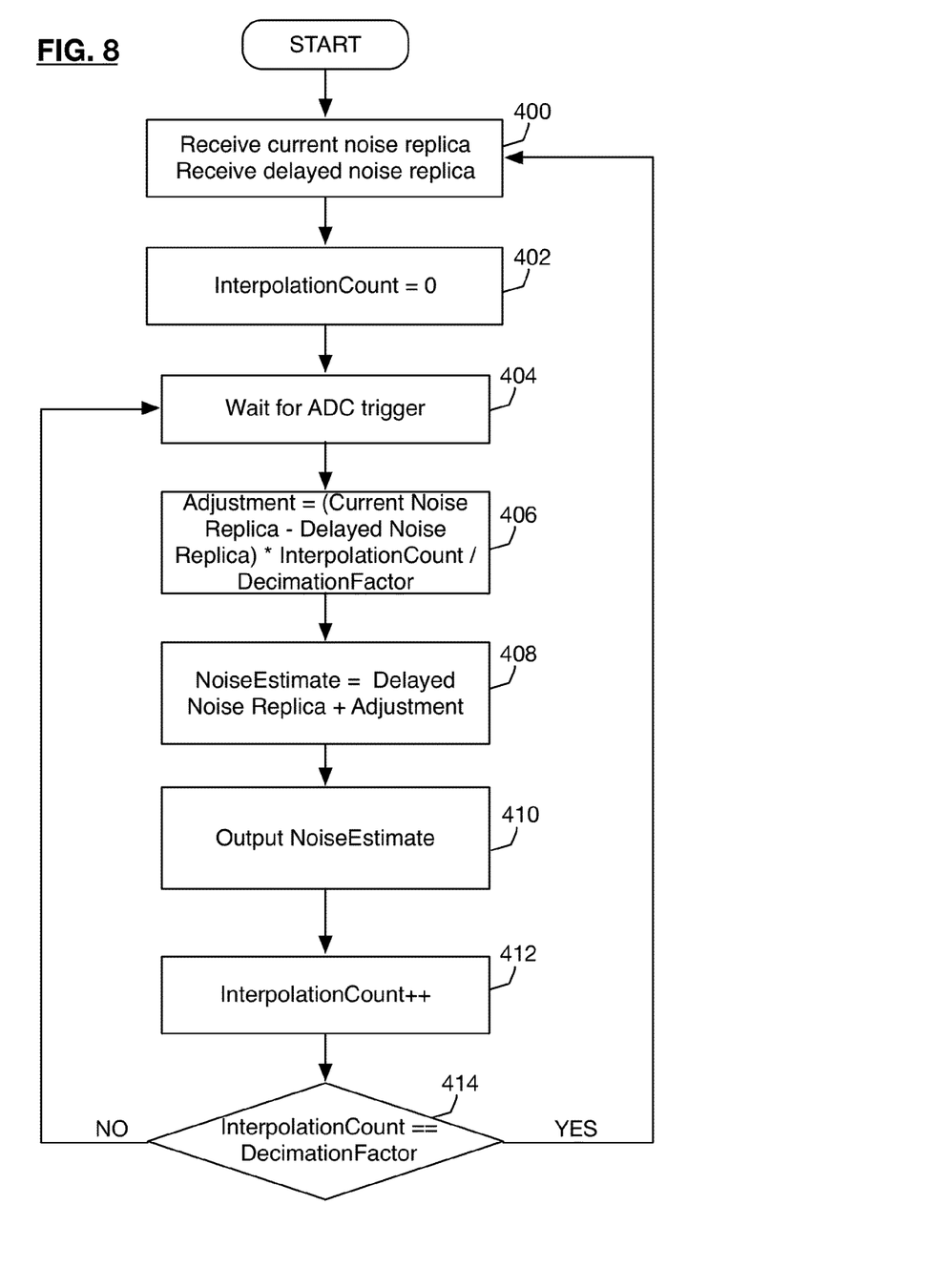
FIG. 8 is a flowchart of processing undertaken by an interpolator of the noise replica generator of FIG. 4 to interpolate between successive noise replicas.

Referring to FIG. 8, at block 400, the interpolator 230 receives from the accumulator 226 a value of the current noise replica, and from the delay 228 a value of delayed noise replica. At block 402, the interpolator 230 sets the value of a variable InterpolationCount to zero. At block 404, the interpolator 230 waits for a trigger that indicates the ADC 202 has generated a sample. In such embodiments, such trigger may be a signal generator by the ADC 202, a voltage at a predetermined pin set by the ADC 202 to a high level or a low level, a flag set by the ADC 202 or another component of the system 100. At block 406, the interpolator 230 calculates the value of a variable Adjust by subtracting the current noise replica from the previous noise replica, and multiplying the result by the value that results from division of the value of variable InterpolationCount and the DecimationFactor. At block 408, the interpolator 230 adds the value of the variable Adjustment to the value of the previous noise replica to develop a value of the variable NoiseEstimate. Thereafter, at block 410, the interpolator 230 provides the value of the variable NoiseEstimate as an estimate of the noise in the current sample generated by the ADC 202 to the Noise Removal Module 206 as an output of the Noise Replica Generator 200. Thereafter, the interpolator 230 increments the value of the variable InterpolationCount at block 412. At block 414, the interpolator 230 determines if the value of the variable InterpolationCount is identical to value of the decimation factor used by the Decimated Sample Generator 220 and, if so, the interpolator 230 proceeds to block 400. Otherwise, the interpolator 230 proceeds to block 404.

Returning to FIG. 3, the Noise Removal Module 206 subtracts the noise estimate developed by the interpolator 230 of the Noise Replica Generator 200 from the sample generated by the ADC 202 to generate a noise corrected sample.

Returning to FIG. 4, in some embodiments, a phase corrector may be used between the accumulator 226 and the interpolator 230 to temporally align the noise replica generated by the accumulator 226 and the sample generated by the ADC. Temporal or phase misalignment may occur, for example, because of delays due to processing time required to generate the noise estimate. In some embodiments, the phase corrector may autocorrelate the zero-crossing signal to which the Decimated Sample Generator 220 is synchronized and the output of the accumulator 226. In other embodiments, a variable delay may be introduced between the accumulator that is adjusted until the phase error between the output frequency of the accumulator 226 and the frequency of the zero-crossing signal generator is minimized. Other ways of aligning the phase of the accumulator 226 with the zero-crossing signal apparent to those who have skill in the art may be used.

Figure 9:
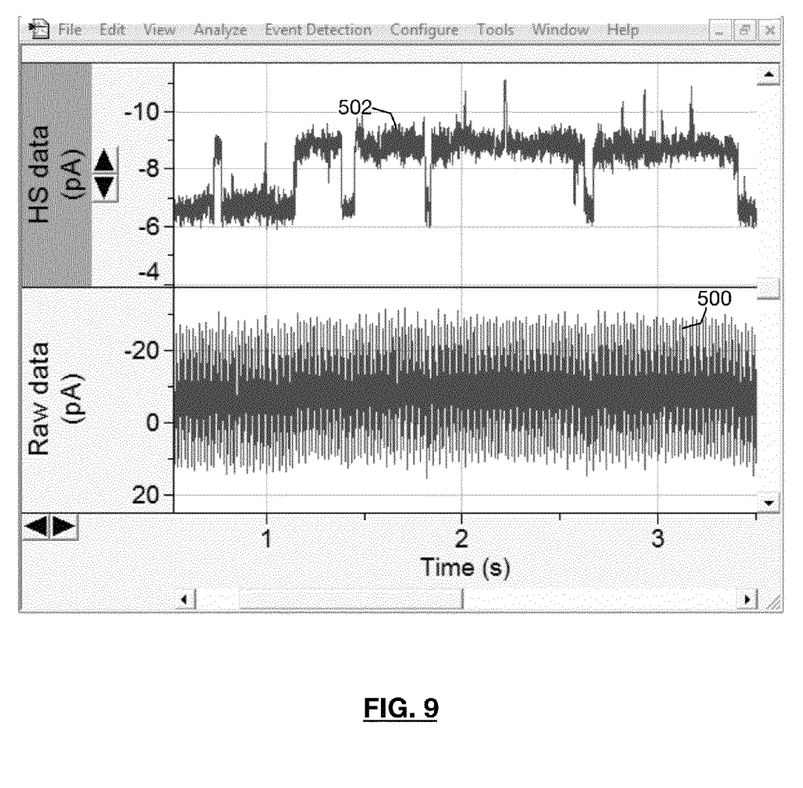
FIGS. 9-11 depict graphs of samples generated by an analog to digital converter of the data acquisition unit of FIG. 3, and noise corrected samples generated by the data acquisition unit of FIG. 3.
Figure 10:
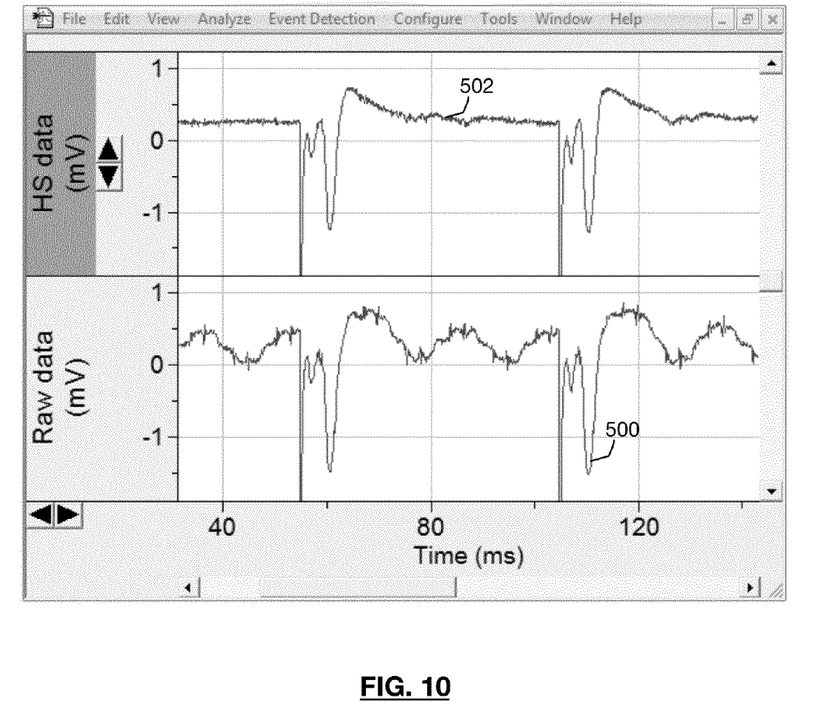
Figure 11:
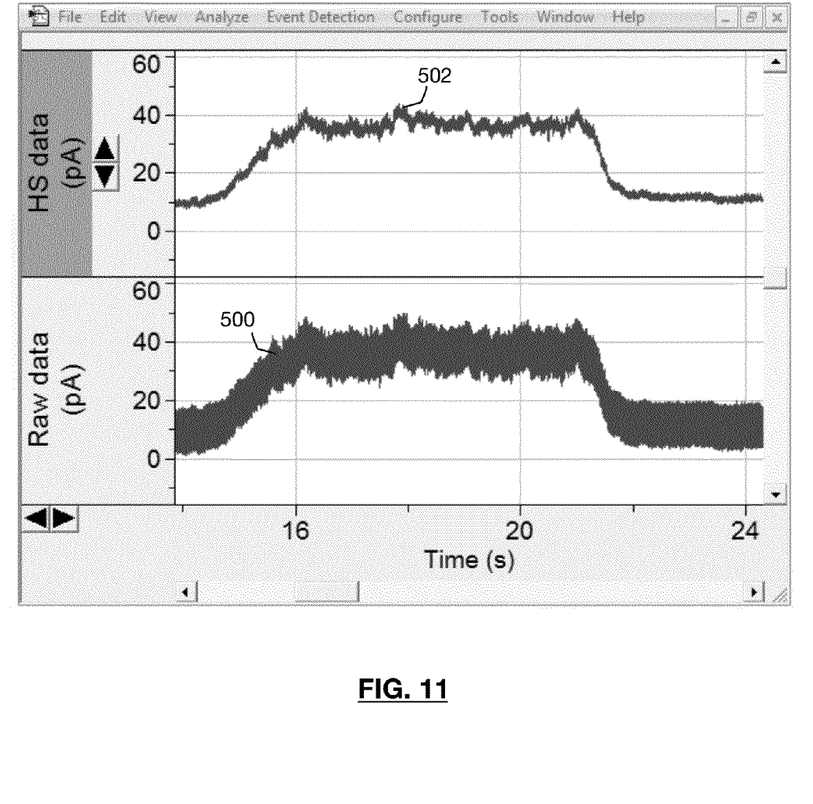

FIGS. 9-11 depict a graph 500 of samples generated by ADC 202 that may be provided to the noise removal block 206. A graph 502 illustrates the noise corrected samples generated by the noise removal block 206 after noise estimates by the noise replica generator 200 are subtracted from the samples shown in the graph 500.

Because the decimated sample generator 220 generates decimated samples at a lower rate than the sampling rate of the ADC 202, the noise replica generator 200 may also generate noise replicas at such lower rate. Therefore, the memory and processing requirements of the noise replica generator 200 may be significantly reduced than if each value generated by the ADC were used to calculate the noise replica.

Compared to ANC systems that estimate noise in the frequency domain, the system 100 disclosed herein corrects noise in the time domain. Typical frequency domain based ANC systems may capture two to three harmonics. In contrast, the time domain based system 100 may be able to capture all harmonics less than the Nyquist frequency that corresponds to a sampling rate of 20 kHz (i.e., less than 10 kHz). One of skill in the art would understand that a frequency domain based system that is able to remove noise in such harmonics may require significantly more memory and processing power than system 100 disclosed herein.

Further, because of the reduced memory and processor requirements of the noise removal processing described herein, the components of the DAU 104 shown in FIG. 3 may implemented in a single field programmable gate array (FPGA) mounted on a printed circuit board.

However, it should be apparent to those who have skill in the art that any combination of hardware and/or software may be used to implement the noise removal processing system described herein. It will be understood and appreciated that one or more of the processes, sub-processes, and process steps described in connection with FIGS. 1-8 may be performed by hardware, software, or a combination of hardware and software on one or more electronic or digitally-controlled devices. The software may reside in a software memory (not shown) in a suitable electronic processing component or system such as, for example, one or more of the functional systems, controllers, devices, components, modules, or sub-modules schematically depicted in FIGS. 1-8. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module or controller (e.g., ADC unit 202, the Zero Crossing Detector 204, the Noise Replica Generator 200 and the Noise Removal Module 206 of FIG. 3), which includes, for example, one or more microprocessors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical).

It will also be understood that receiving and transmitting of signals as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

INDUSTRIAL APPLICABILITY

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. It should be understood that the illustrated embodiments are exemplary only, and should not be taken as limiting the scope of the disclosure.

We claim:

1. A data acquisition system coupled to a first mains power source, comprising:
   a test probe that generates a signal, wherein the signal comprises a noise component that is synchronous with the first mains power source;
   a zero crossing detector that generates a cycle start signal in accordance with a voltage of the first mains power source;
   an analog to digital converter, wherein the analog-to-digital converter samples the signal provided by the test probe and generates data samples at a sampling rate;
   a noise replica generator that generates noise replicas from the data samples at a replica generation rate and noise estimates from the noise replicas at the sampling rate, wherein the replica generation rate is less than the sampling rate; and
   a noise removal module that removes each noise estimate from a corresponding data sample, wherein the noise estimate represents the noise component in the data sample.

2. The data acquisition system of claim 1, wherein the data acquisition system automatically adapts to changes in a first power line frequency of the first mains power source.

3. The data acquisition system of claim 1, wherein the data acquisition system may be operated with the first mains power source that supplies power at a first power line frequency, and then be operated without modification with a second mains power source that supplies power at a second power line frequency.

4. The data acquisition system of claim 1, wherein the noise replica generator includes a decimated sample generator, wherein the decimated sample generator generates a decimated sample from the data samples at the replica generation rate.

5. The data acquisition system of claim 4, wherein the noise replica generator operates in synchronism with the cycle start signal.

6. The data acquisition system of claim 5, wherein the noise replica generator includes an accumulator, wherein the accumulator includes a predetermined number of buffers, each buffer holds decimated samples generated during a periodic cycle of the first mains power source, wherein the start and end of the periodic cycle are indicated by successive cycle start signals.

7. The data acquisition system of claim 6, wherein the decimated samples held in each of the buffers contribute to the noise replica.

8. The data acquisition system of claim 6, wherein the noise replica generator includes a DC offset calculator that calculates an average of the decimated samples generated during the periodic cycle.

9. The data acquisition system of claim 1, wherein the noise replica generator includes an interpolator that interpolates between successive noise replicas generated at the replica generation rate to develop noise estimates at the sampling rate.

10. The data acquisition system of claim 1, wherein the test probe is coupled to a biological subject.

11. A method for operating a data acquisition system coupled to a first mains power source, comprising:
    receiving a signal from a test probe, wherein the signal comprises a noise component that is synchronous the first mains power source;
    generating a cycle start signal in accordance with a voltage of the first mains power source;
    sampling the signal from the test probe to generate data samples of the signal at a sampling rate;
    generating noise replicas from the data samples at a replica generation rate, wherein the replica generation rate is less than the sampling rate;
    developing noise estimates from the noise replicas at the sampling rate; and
    subtracting each noise estimate from a corresponding data sample, wherein the noise estimate represents the noise component in the data sample.

12. The method of claim 11, further comprising automatically adapting the data acquisition system to changes in a first power line frequency of the mains power source.

13. The method of claim 12, further comprising operating the data acquisition system with both the first mains power source that supplies power at a first power line frequency, and then a second mains power source that supplies power at a second power line frequency without modification.

14. The method of claim 13, further comprising decimating the data samples to generate decimated samples at the replica generation rate.

15. The method of claim 14, further comprising synchronizing generation of the noise replicas with the cycle start signal.

16. The method of claim 15, further comprising accumulating the decimated samples in a plurality of buffers, wherein each buffer stores decimated samples generated during a periodic cycle of the mains power source, wherein the start and end of the periodic cycle are indicated by successive cycle start signals.

17. The method of claim 16, further comprising developing a noise replica using the decimated samples held in each of the buffers.

18. The method of claim 16, further comprising calculating an average of the decimated samples generated during the periodic cycle.

19. The method of claim 11, further comprising interpolating between successive noise replicas generated at the second frequency to develop noise estimates at the sampling rate.

20. The method of claim 11, wherein receiving a signal from the test probe includes receiving a signal from a biological subject.

* * * * *